US00PP26607P2

(12) United States Plant Patent
Garner

(10) Patent No.: US PP26,607 P2
(45) Date of Patent: Apr. 12, 2016

(54) ***ALOCASIA* PLANT NAMED 'TINY DANCERS'**

(50) Latin Name: ***Alocasia brisbanensis*×*Alocasia odora***
Varietal Denomination: Tiny Dancers

(71) Applicant: LariAnn Garner, Florida City, FL (US)

(72) Inventor: LariAnn Garner, Florida City, FL (US)

( * ) Notice: Subject to any disclaimer, the term of this patent is extended or adjusted under 35 U.S.C. 154(b) by 240 days.

(21) Appl. No.: 13/998,642

(22) Filed: Nov. 19, 2013

(51) Int. Cl.
*A01H 5/12* (2006.01)

(52) U.S. Cl.
USPC ..... Plt./373

(58) Field of Classification Search
USPC ..... Plt./373
See application file for complete search history.

(56) References Cited

PUBLICATIONS

Aroidia—The Hybrid Files, aroidiaresearch.org/hybrids.htm, pulled from the internet on Sep. 9, 2015.*

* cited by examiner

*Primary Examiner* — Anne Grunberg
(74) *Attorney, Agent, or Firm* — Penny J. Aguirre

(57) ABSTRACT

A new cultivar of *Alocasia* plant named 'Tiny Dancers' that is characterized by its very dwarf plant habit, its leaves that are uniquely teardrop in shape, its long, delicate petioles, its significantly increased number of leaves at maturity than either of its parents, and its inability to bloom or set seed.

2 Drawing Sheets

Botanical classification: *Alocasia brisbanensis*×*Alocasia odora.*

Cultivar designation: 'Tiny Dancers'.

BACKGROUND OF THE INVENTION

The present invention, *Alocasia* 'Tiny Dancers', relates to a new and distinct interspecific hybrid of *Alocasia*, hereinafter referred to by its cultivar name, 'Tiny Dancers'. 'Tiny Dancers' is a new tropical plant used as a landscape and container plant.

The new cultivar was derived from a controlled breeding program conducted by the Inventor at his nursery in Florida City, Fla., USA. 'Tiny Dancers' arose from a cross make in 2009 between an unnamed plant of *Alocasia brisbanensis* as the female parent and an unnamed plant of *Alocasia odora* as the male parent. 'Tiny Dancers' was selected as a single unique plant in 2010 from amongst the seedlings derived from the above cross.

Asexual propagation of the new cultivar was first accomplished by division by the Inventor in Florida City, Fla. in 2011. Asexual propagation of 'Tiny Dancers' by division and tissue culture has shown that the unique features of the new cultivar are stable and reproduced true to type in successive generations.

SUMMARY OF THE INVENTION

The following traits have been repeatedly observed and represent the characteristics of the new cultivar. These attributes in combination distinguish 'Tiny Dancers' as a new and unique cultivar of *Alocasia.*

1. 'Tiny Dancers' exhibits a very dwarf plant habit.
2. 'Tiny Dancers' exhibits leaves that are uniquely teardrop in shape.
3. 'Tiny Dancers' exhibits long, delicate petioles.

4. 'Tiny Dancers' exhibits a significantly increased number of leaves at maturity than either of its parents.
5. 'Tiny Dancers' is non-blooming and therefore does not set seed.

The female parent of 'Tiny Dancers', an unnamed plant of *Alocasia brisbanensis*, differs from 'Tiny Dancers' in having a much larger plant habit, in having larger, broader leaves that are elliptical in shape, in having a decreased number of leaves at maturity, and in having thicker, heavier petioles. The male parent of 'Tiny Dancers', an unnamed plant of *Alocasia odora*, differs from 'Tiny Dancers' in having a much larger plant habit, in having larger, broader leaves that are elliptic-ovate in shape, in having a decreased number of leaves at maturity, and in having thicker, heavier petioles. 'Tiny Dancers' can be most closely compared to typical plants of the species *Alocasia cucullata* and typical plants of the species *Alocasia odora*. Typical plants of *Alocasia cucullata* are similar to 'Tiny Dancers' in having similarly shaped leaves. Typical plants of *Alocasia cucullata* differ from 'Tiny Dancers' in having a much larger plant habit, in having leaves that are larger and broader, in having a decreased number of leaves at maturity, and in having flowers with fertile pollen. Typical plants of *Alocasia odora* are similar to 'Tiny Dancers' in having similarly shaped leaves. Typical plants of *Alocasia odora* differ from 'Tiny Dancers' in having a much larger plant habit, in having leaves that are larger and broader, in having a decreased number of leaves at maturity, and in having flowers with fertile pollen. 'Tiny Dancers' can also be compared to *Alocasia odora* 'Variegata' (not patented), which differs in the above characteristics for *Alocasia odora* and in having variegated foliage and the *Alocasia brisbanensis*×*Alocasia odora* cultivar 'Bisbane Blue' (not patented), which differs from 'Tiny Dancers' in having leaves that are more puckered and in having a much larger plant size and larger leaf blades.

BRIEF DESCRIPTION OF THE DRAWING

The accompanying colored photographs illustrate the overall appearance and distinct characteristics of the new *Aloca-*

*sia*, 'Tiny Dancers'. The photographs were taken of a 15 month-old plant of 'Tiny Dancers' as grown in a greenhouse in a 1-gallon container in Florida City, Fla.

Figure 1:
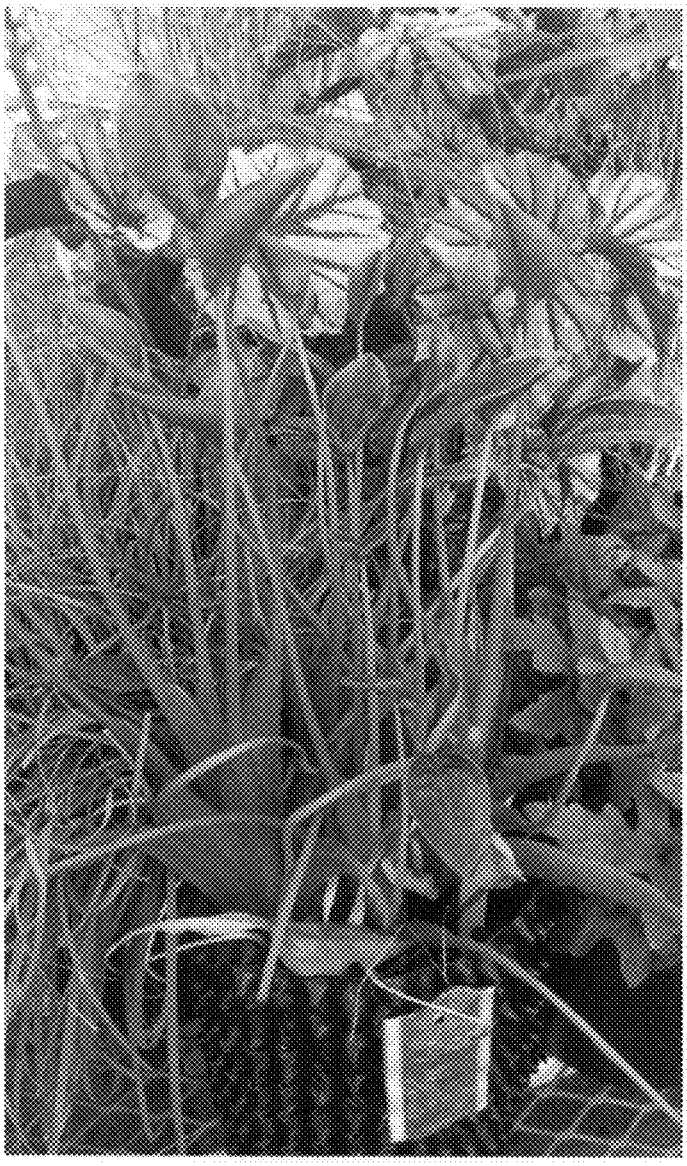
FIG. 1 provides an overall view of the foliage and plant habit of 'Tiny Dancers'.
Figure 2:
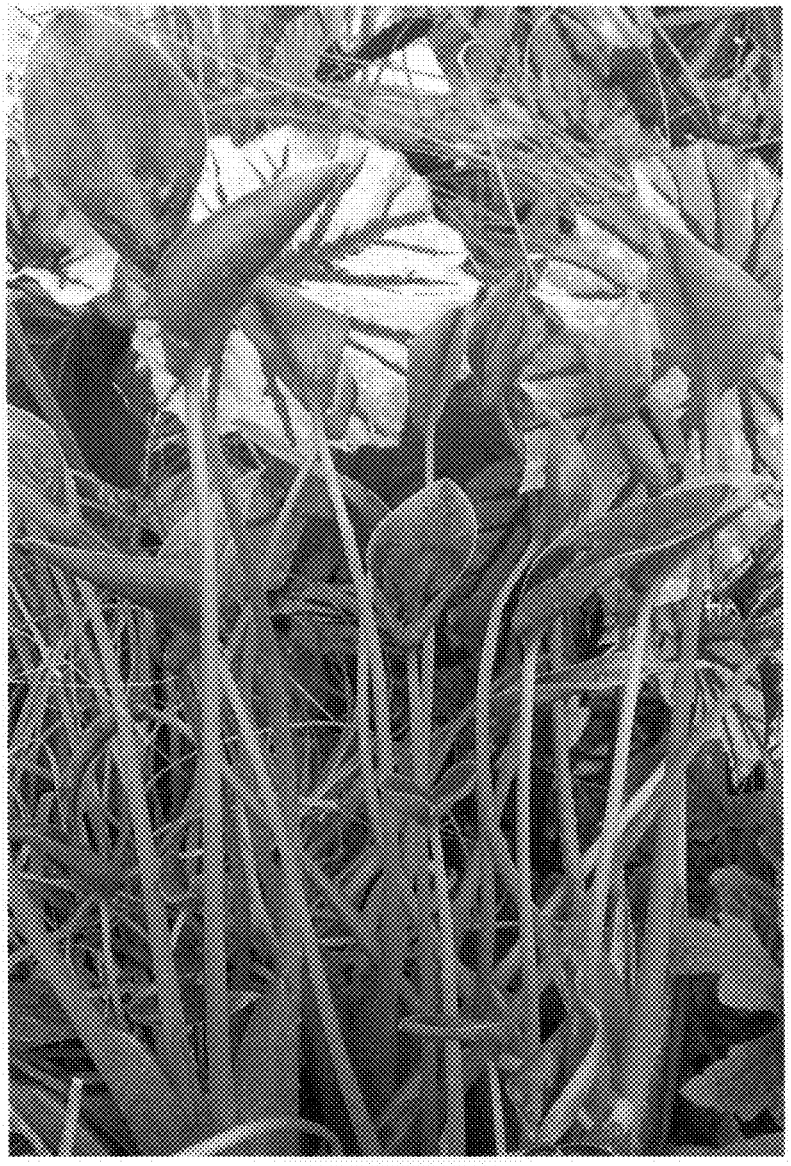

The photograph in FIG. 2 provides a close-up view of the leaves of 'Tiny Dancers'.

The colors in the photographs are as close as possible with the photographic and printing technology utilized and the color values cited in the Detailed Botanical Description accurately describe the colors of the new *Alocasia*.

DETAILED BOTANICAL DESCRIPTION OF THE PLANT

The following is a detailed description of three month-old plants of the new cultivar as grown in a 4-inch containers outdoors in a greenhouse in Florida City, Fla. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Tropical perennial herb.

*Plant habit.*—Upright, stemless, very dwarf with numerous leaves.

*Height and spread.*—Reaches about 45 cm in height and 30 cm in width.

*Cold hardiness.*—Tropical, tender to cold.

*Diseases and pests.*—Not more susceptible to pests and diseases than other *Alocasia* varieties.

*Roots.*—Fleshy (161D in color) and arising from rhizomes; an average of 6 cm in length and 1.5 cm in width, 138B in color with horizontal ridges 200A.

*Propagation type.*—Division, tissue culture.

*Growth rate.*—Moderate.

*Stem description.*—Stemless.

Foliage description:

*Leaf shape.*—Cordate-sagittate (tear-drop).

*Leaf division.*—Single.

*Leaf base.*—Sagittate, deeply cut, curled inward.

*Leaf apex.*—Cuspidate.

*Leaf venation.*—Pinnate, color: upper surface matches leaf color, lower surface is 139A.

*Leaf margins.*—Entire.

*Leaf attachment.*—Petiolate.

*Leaf arrangement.*—Alternate.

*Lear number.*—An average of 6 leaves per rhizome division, an average of 18 per plant as grown in a 4-inch container.

*Leaf surface.*—Upper surface; coriaceous, glabrous and satiny, lower surface; glabrous and very glossy.

*Leaf orientation.*—Held at a 45° angle.

*Leaf color.*—Young upper and lower surface a blend of 144A and 137C, mature foliage: upper surface; a blend of 137A and N137A, lower surface; a blend of 146A and 147B.

*Leaf size.*—Up to 7 cm in length and about 4 cm in width.

*Petioles.*—Held erect to semi-erect, about 9 cm in length and 3 mm in diameter and about 5 mm in diameter near base, glabrous surface, 144B in color blending with 137B near base, winged near base; an average of 3 cm in length and 5 mm in width (on a petiole 9 cm in length), a blend of 137B and 138B in color, both surfaces are glabrous with the inner surface satiny.

Inflorescence description: Plants of the new cultivar do not produce blooms and therefore do not set seed.

It is claimed:

1. A new and distinct cultivar of *Alocasia* plant named 'Tiny Dancers' as herein illustrated and described.

* * * * *